(12) United States Patent
Moore

(10) Patent No.: US 7,614,315 B2
(45) Date of Patent: Nov. 10, 2009

(54) SORBENT TRAP CARTRIDGE FOR MERCURY EMISSIONS MONITORING

(75) Inventor: Randall Moore, Powell, TN (US)

(73) Assignee: Shaw Intellectual Property Holdings, Inc., Baton Rouge, LA (US)

(*) Notice: Subject to any disclaimer, the term of this patent is extended or adjusted under 35 U.S.C. 154(b) by 148 days.

(21) Appl. No.: 12/031,980

(22) Filed: Feb. 15, 2008

(65) Prior Publication Data

US 2008/0202207 A1  Aug. 28, 2008

Related U.S. Application Data

(60) Provisional application No. 60/901,766, filed on Feb. 16, 2007.

(51) Int. Cl.
 G01N 1/22  (2006.01)
 G01N 1/00  (2006.01)
 G01N 30/96 (2006.01)

(52) U.S. Cl. ............... 73/863.21; 422/88; 436/81; 73/863.81; 73/863.12

(58) Field of Classification Search .......... 73/23.1, 73/863.11, 863.21, 863.71, 863.81, 864.81, 73/864.84, 864.85, 866, 866.5; 422/88; 436/81
See application file for complete search history.

(56) References Cited

U.S. PATENT DOCUMENTS

| 2,345,090 | A | | 3/1944 | Brace |
|---|---|---|---|---|
| 3,711,248 | A | | 1/1973 | Coffey |
| 4,000,918 | A | * | 1/1977 | Reker ..................... 285/93 |
| 4,161,883 | A | * | 7/1979 | Laird et al. ............ 73/863.24 |
| 5,597,535 | A | | 1/1997 | Schaedlich et al. |
| 5,660,795 | A | | 8/1997 | Schaedlich et al. |
| 6,200,816 | B1 | | 3/2001 | Farber et al. |
| 6,223,584 | B1 | * | 5/2001 | Mustacich et al. ........ 73/23.41 |
| 6,475,802 | B2 | | 11/2002 | Schaedlich et al. |
| 6,619,143 | B2 | * | 9/2003 | Danylewych-May et al. ................... 73/863.21 |
| 6,736,883 | B2 | | 5/2004 | Sjostrom et al. |
| 6,869,800 | B2 | * | 3/2005 | Torgerson et al. ............ 436/37 |
| 7,568,401 | B1 | * | 8/2009 | Berends, Jr. ............ 73/863.21 |
| 2005/0084976 | A1 | | 4/2005 | Baldwin et al. |
| 2006/0245973 | A1 | | 11/2006 | Kita et al. |
| 2009/0084198 | A1 | * | 4/2009 | Wright et al. ............ 73/863.12 |
| 2009/0084199 | A1 | * | 4/2009 | Wright et al. ............ 73/863.82 |

OTHER PUBLICATIONS

"The Real Scoop About Appendix K." CATM Technical Newsletter 12 (2006): 3, 4.
"Apex Source Testing Equipment Instruments." Apex Instruments, Inc.. May 14, 2008 <www.apexinst.com/products/mercury-xc6000epc.htm>.

* cited by examiner

*Primary Examiner*—Lisa M Caputo
*Assistant Examiner*—Punam Patel
(74) *Attorney, Agent, or Firm*—Kean Miller Hawthorne D'Armond McCowan & Jarman, LLP

(57) ABSTRACT

A probe for measuring mercury emissions in a flue gas. The probe contains a novel cartridge for holding one or more sorbent traps, which cartridge is easily removed and inserted on-site with reduced danger of sorbent trap damage.

7 Claims, 3 Drawing Sheets

Figure 4
Figure 5
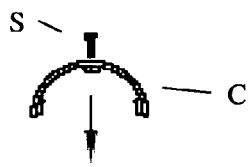
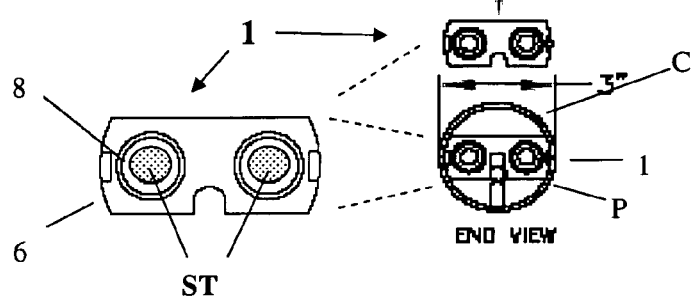
Figure 6
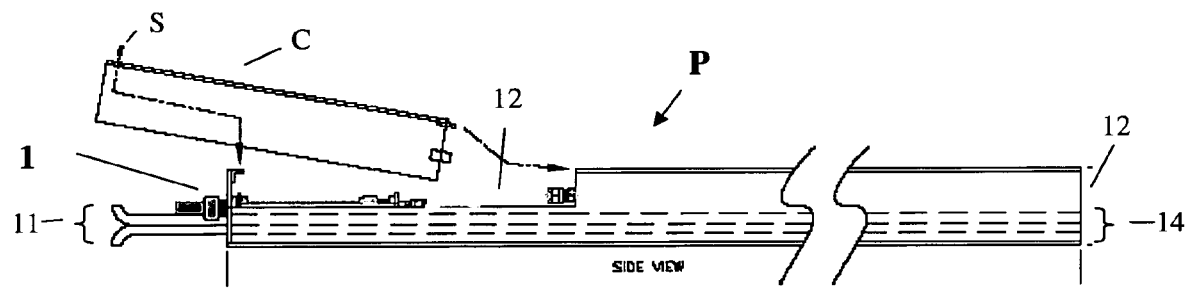
Figure 7
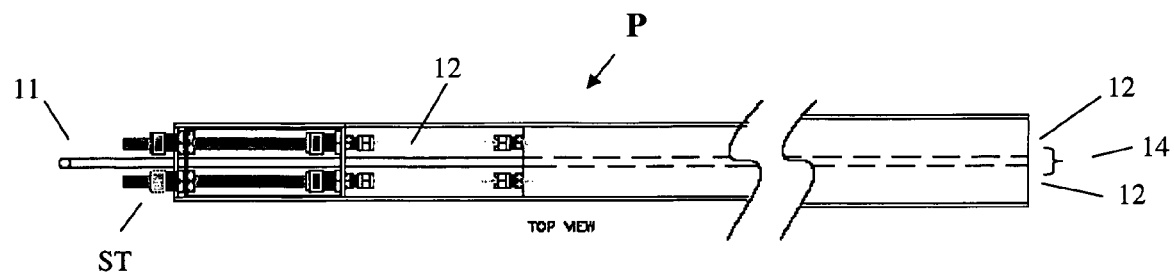

SORBENT TRAP CARTRIDGE FOR MERCURY EMISSIONS MONITORING

CROSS REFERENCE TO RELATED APPLICATIONS

This application is based on Provisional Application 60/901,766 filed Feb. 16, 2007.

FIELD OF INVENTION

The present invention relates to a probe for measuring mercury emissions in a flue gas. The probe contains a novel cartridge for holding one or more sorbent traps, which cartridge is easily removed and inserted on-site with reduced danger of sorbent trap damage.

BACKGROUND OF THE INVENTION

Mercury emissions from various industries has become a serious environmental issue. The largest sources of mercury emissions in the US are utility boilers, followed by waste incinerators that combust mercury-containing wastes (municipal and medical), coal-fired industrial boilers, and cement kilns that combust coal-fired fuels. Other potentially important sources of mercury emissions are manufacturing plants and basic chemical processes. One particularly notable source of mercury emissions is coal-fired power plants. These plants emit large amounts of mercury each year, and will be required to reduce their emissions level by greater than 90% by 2010. Consequently, mercury is listed by the International Program of Chemical Safety as one of the most dangerous chemicals in the environment.

Vapor phase mercury settles over waterways, polluting rivers and lakes, and contaminating fish. Further, exposure to mercury poses real risks to public health, especially to children and developing fetuses. Exposure to mercury has been associated with both neurological and developmental damage in humans. The developing fetus is the most sensitive to mercury's effects, which include damage to nervous system development. People are exposed to mercury primarily through eating fish that have been contaminated when mercury from power plants and other sources is deposited to water bodies. Once mercury enters water, biological processes can transform it into methylmercury, a highly toxic form of mercury that builds up in animal and human tissues. In fact, methylmercury can accumulate in some fish in concentrations thousands of times higher than in the waters they live in, which is why state environmental regulatory agencies often issue fish-consumption advisories. As previously mentioned, the greatest source of mercury emissions is power plants, and historically they have not been required to control these emissions until recently.

As part of the Clean Air Mercury Rule (CAMR), power plants will soon be required to measure mercury emissions on a continuous basis. There are three forms of mercury in stack (flue) gas from a coal-fired power plant that can potentially be monitored by a mercury monitoring system, namely $Hg^0$, oxidized $Hg^{+2}$, and particulate bound Hg of either species, at stack gas temperatures in excess of 200° F. However, the Environmental Protection Agency (EPA) does not currently require the continuous monitoring of particulate bound $Hg^0$. Accordingly, total mercury for monitoring in accordance with EPA regulations, i.e. gaseous mercury is the sum of elemental mercury ($Hg^0$) and oxidized mercury ($Hg^{++}$). One leading method of measuring mercury emissions on a continuous basis is to capture the mercury in a bed of sorbent (40 CFR, Part 75), following the procedures outlined in Appendix K of the CAMR. Appendix K is a set of protocols and stated criteria that must be met to in order for the U.S Environmental Protection Agency (EPA) to consider the method valid. While continuous emissions monitoring is required for mercury testing from a stack gas there is also a requirement for a backup system using dual sorbent traps.

Samples of stack gas are usually taken by inserting a probe into the stack at a predetermined location and for a predetermined length of time to complete a test cycle. The probe can be one wherein stack gas is continuously conducted through the probe to an analytical device designed to measure mercury. The analytical device can be either in the proximity of the probe or at ground location. The probe can also be one that contains a sorbent trap at its tip extending into the stack so that as stack gas is conducted through the probe mercury is captured on the sorbent in the trap. The flue gas sample is then dried and expelled into the atmosphere. If sorbent traps are used the probe will be removed from the stack and the sorbent traps removed for analytical testing at the end of a test cycle. Fresh sorbent traps are then inserted in the probe and the probe reinserted in the stack for further sampling.

There are several disadvantages associated with the use of conventional sorbent trap/probe equipment. For example, the probe which typically weights about 100 lbs is generally inserted into a stack several hundred feet off the ground. Thus, it is often difficult and cumbersome for a technician working on a narrow platform several hundred feet off the ground to remove the probe and safely change-out the sorbent traps. There is always the danger that the sorbent traps, which typically extend past the end of the probe will be broken in event the probe inadvertently hits an object while the probe is being inserted or removed from the stack. Therefore there is a need in the art for improved equipment and techniques that lessen the danger of damage to the sorbent traps during insertion and removal of a probe, containing one or more sorbent traps, from a stack.

SUMMARY OF THE INVENTION

In accordance with the present invention there is provided a probe for measuring the concentration of mercury in a flue gas in a stack, which probe comprising:

a) a housing of a suitable geometric shape having a first end adapted to be situated in a stack and a second end adapted to be external thereto, b) at least one sorbent trap containing a media capable of capturing mercury when and flue gas stream is passed therethrough, which one or more cylindrical sorbent traps are held in a cartridge having a front end and a back end and sides and whose top and bottom are open and which cartridge is located within the first end of said probe so that said at least one cylindrical sorbent trap is in fluid communication with the flue gas stream within the stack and a receiving tube within the probe housing; and c) a receiving container, preferably a tube, located within said housing having a first end fluidly connected to the cartridge and sorbent traps and a second end extending from the second end of said housing.

BRIEF DESCRIPTION OF THE FIGURES

FIG. 4 hereof is an end view of a sorbent trap cartridge of the present invention.

FIG. 5 is an end view of a probe of the present invention showing the removable cover and sorbent trap cartridge in an exploded section upper section and the assembled view at the lower section FIG. 6 hereof is a side view of a probe containing the sorbent trap cartridge of the present invention.

FIG. 7 hereof is a top view of a probe containing the sorbent trap cartridge and two sorbent traps of the present invention.

DETAILED DESCRIPTION OF THE INVENTION

Figure 1:
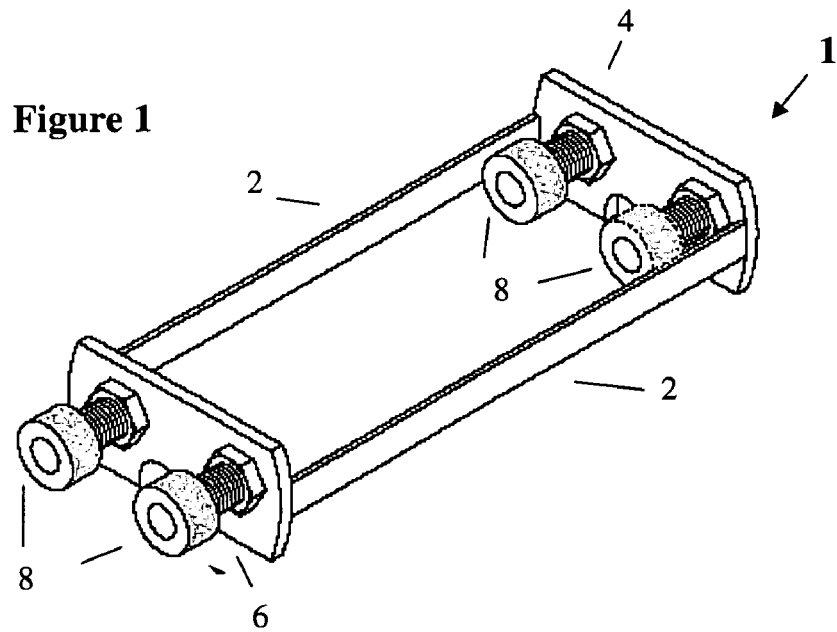
FIG. 1 hereof is a perspective view of a sorbent trap cartridge of the present invention.

The term "stack gas" as used herein is as it is generally known in the art. It is typically a gas that exits to the atmosphere via a flue, or stack, which is a pipe or channel for conveying exhaust gases from a source such as a fireplace, furnace, boiler or generator. The terms "flue gas" and "stack gas" are used interchangeably herein. A preferred source of flue gas, to be treated in accordance with the present invention, is from power plants, including coal-fired plants. The composition of the flue gas will depend on what is burned, but it will typically be comprised of predominantly carbon dioxide, water vapor, heated air and minor amounts of pollutants, such as particulate matter, carbon monoxide, nitrogen oxides, sulfur oxides, mercury moieties, and ammonia.

This invention is directed to the sorbent trap method for obtaining mercury samples from flue gases. The sorbent trap monitoring system typically includes EPA required equipment such as: a probe, paired sorbent traps, automated data acquisition and handling system, moisture removal components, sample pump, dry gas meter and heated umbilical line. The monitoring system samples flue gas at a rate proportional to the flue gas volumetric flow rate. Sampling is a batch process. Mercury mass emissions per hour during the sampling period are calculated in conjunction with contemporaneous hourly measurements of the corrected flue gas flow rate. Each system requires the use of paired sorbent traps. Each trap contains a main section, a backup section, and a third section to allow spiking with a calibration gas of known mercury concentration. A certified flow monitoring system and correction for flue gas moisture content are also required. The hourly mercury mass emissions for each collection period are determined using the results of the analyses in conjunction with contemporaneous hourly data recorded by a certified stack flow monitor. For each pair of sorbent traps analyzed, the average of the two mercury concentrations are used for reporting purposes.

The sorbent media, which will generally be a carbon material such as coconut shell charcoal, used to collect mercury must be configured in a trap using three distinct and identical sections, which are amenable to separate analyses. These sections, as previously mentioned are a first section that is for the primary capture of gaseous mercury. The second, or secondary section, is for the determination of mercury breakthrough, which must be less than or equal to 5% of total mercury. The third section is a section spiked with a known amount of mercury prior to sampling for determining recovery efficiency. Mercury recovery must be between 75% to 125% of spiked mercury. For conventional probes, one or more, preferably two, sorbent traps will be inserted into the tip of probe then inserted into the stack for sampling.

The present invention is directed to a probe and sorbent trap holder having the advantage of safe and efficient handling for on-site sorbent trap change-out. Conventional practice requires that the probe be removed from the stack and the sorbent trap(s) be individually removed from the probe and stored in a safe container for subsequent analysis for mercury. A new one or more sorbent traps is inserted into the end of the probe and the probe reinserted into the stack through a suitable port. As previously mentioned such a conventional method has the disadvantage of exposing the sorbent trap, which is typically a quartz tube filled with sorbent media, to damage during the change-out process. The present invention is directed to a holder, or cartridge, for storing the sorbent traps prior to, during, and after flue gas sampling. The present invention is also directed to an improved probe for mercury sampling.

FIG. 1 hereof is a perspective view of a sorbent trap cartridge 1 of the present invention having an open top and open bottom. The sorbent trap cartridge 1 is comprised of a frame having sides 2 and a back end plate 4 and a front end plate 6. Both end plates contain a pair of suitable fitting, such as knurled nut fittings 8 at the upstream side of the plate. Any other suitable fitting can be used, such as a slide fitting with is well known in the art. By "upstream" we mean with respect to the flow of flue gas sample into the probe via the sorbent traps. The length of sides 2 will be of a predetermined length to accommodate a predetermined sorbent trap. The opening of the knurled nut fittings will of suitable diameter to accommodate sorbent traps of predetermined diameter.

Figure 2:
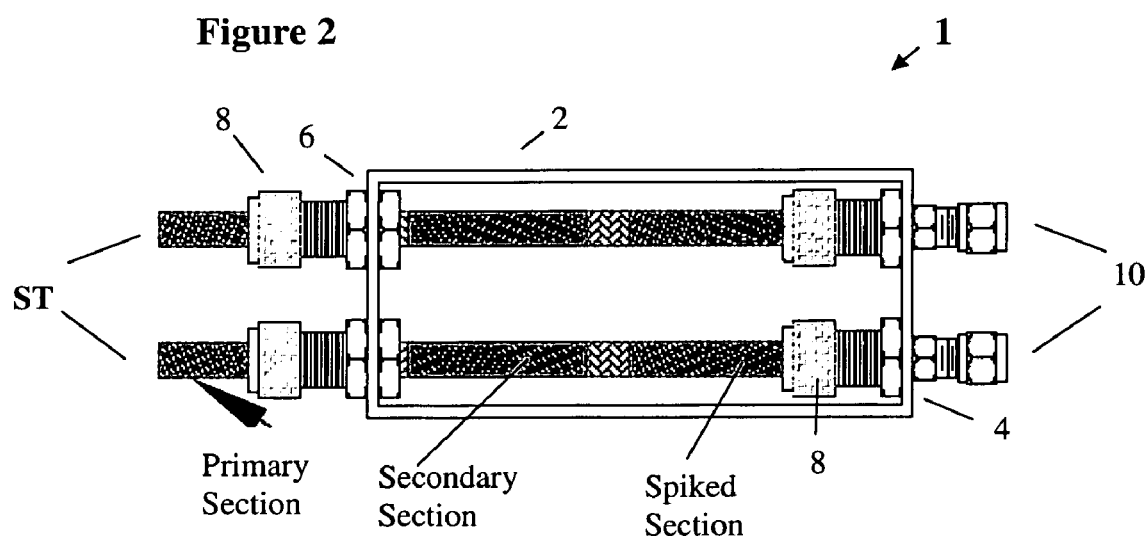
FIG. 2 hereof is a plan view of a sorbent trap cartridge of the present invention containing two sorbent traps.

FIG. 2 hereof is a plan view of a sorbent trap cartridge 1 of the present invention holding two sorbent traps ST. As previously mentioned the sorbent traps will generally be quartz tubes containing the sorbent media, which is preferably a carbon material, more preferably an iodated carbon material. The sorbent traps ST shown in this FIG. 2 are quartz tubes containing three samples sections of carbon material. The first, or primary, section is the main section for sorbing mercury from the flue gas whereas the secondary section is used to determine mercury breakthrough. The third, or spiked section, contains a known concentration of mercury. Sorbent trap cartridge 1 contains connecting means 10 for connection to receiving tubes within an umbilical line, not shown.

Figure 3:
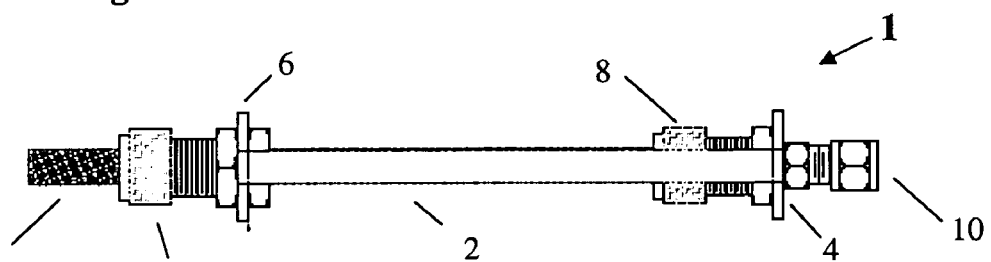
FIG. 3 hereof is a side view of a sorbent trap cartridge of the present invention.

FIG. 3 hereof is a side view of the sorbent trap cartridge 1 of the present invention wherein all numbered elements are as in FIGS. 1 and 2 hereof.

FIG. 4 hereof is a front view of the sorbent cartridge 1 of FIG. 2 hereof containing two sorbent traps ST. All elements and element numbers are as indicated in FIGS. 1-3 hereof.

FIG. 5 hereof is an exploded end view of the end of a sampling probe P containing a sorbent trap cartridge 1 of the present invention. Sorbent trap cartridge cover C is removable to allow cartridge 1 to be inserted and removed from the probe.

FIG. 6 hereof is a side view of a sampling probe P of the present invention showing removable cover C and sorbent trap cartridge 1 inserted in the probe P and fluidly attaching it to gas receiving tubes 12. 14 represent a plurality of other communication links, such as tubes, thermocouple wires, power wires, and messenger wires for relaying predetermined information from the probe, through an umbilical line (not shown) and to one or more controllers, analyzers, and central processing units. Cover C, when in place is secured to the probe by any conventional suitable means, such as by use of one or two screws at location S. 11 represents a low pressure and a high pressure pilot port. FIG. 7 is a top view of a probe P of FIG. 6 hereof, but with the cover removed. This figure shows two sorbent traps ST positioned in probe P and fluidly attached to receiving tubes 12.

Figure 8:
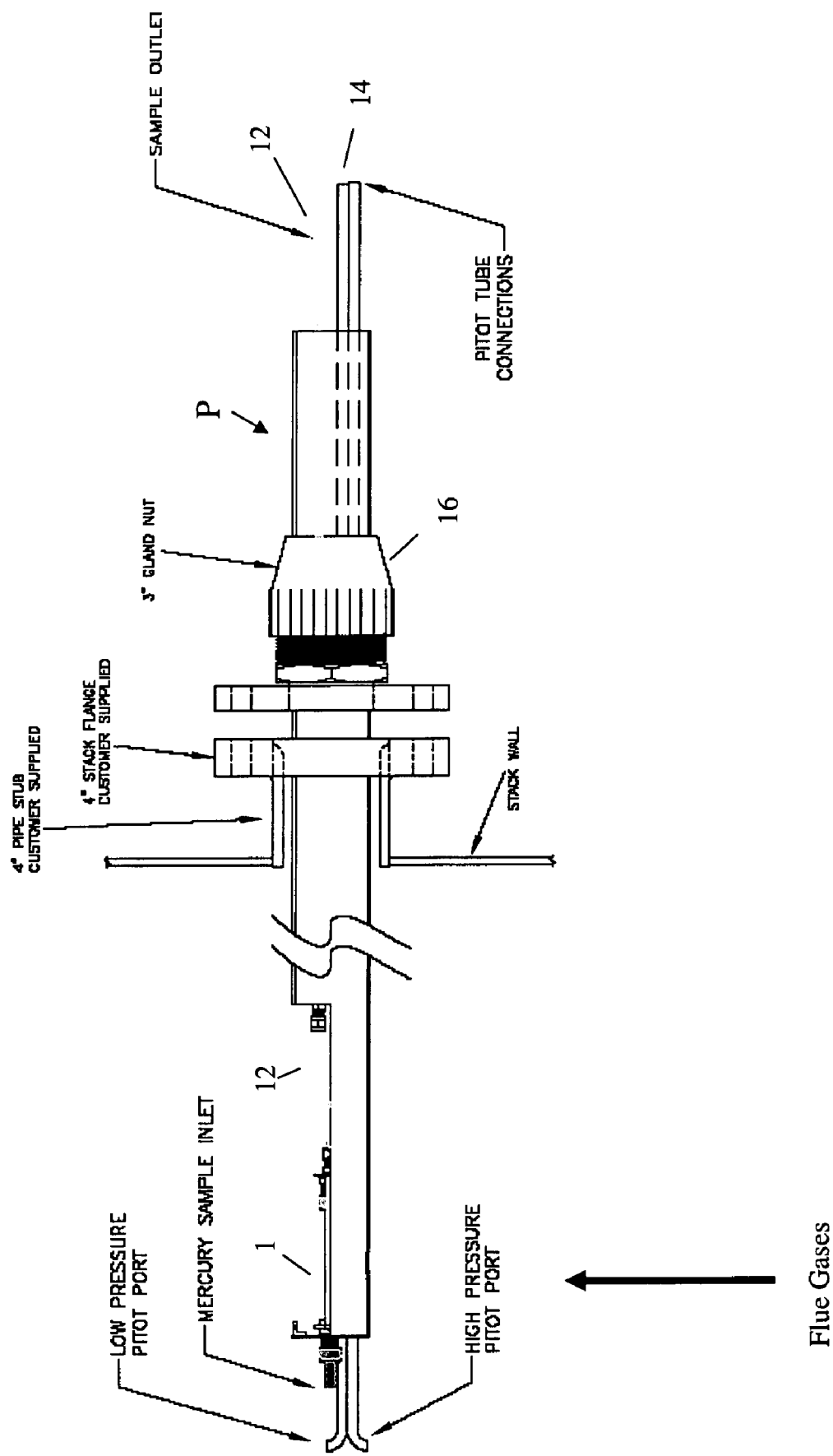
FIG. 8 hereof is a side view of a probe containing a sorbent trap cartridge inserted through, a sampling port of a stack for measuring mercury in a stack gas.

FIG. 8 shows a probe of the present invention inserted in a stack for receiving samples of flue gas. Probe P is inserted in the stack through a port, typically referred to as a pipe stub of suitable diameter to receive the probe. The probe is securely held in place by use of a suitable leak tight connection, such as a flange and gland nut 16 arrangement as shown.

While the foregoing specification sets forth preferred embodiments of the present invention for the purposes of illustrating the present invention, it will be understood that such embodiments may be widely varied by those having skill in the art without departing from the spirit or of the present invention.

What is claimed is:

1. A probe for measuring the concentration of mercury in a flue gas in a stack, which probe comprises:
    a) a housing having a first end adapted to be situated in a stack and a second end adapted to be external thereto,
    b) at least one sorbent trap containing a media capable of capturing mercury when a flue gas stream is passed there-through, which the at least one sorbent trap is held in a cartridge forming a frame having a front end and a back end and side walls and whose top and bottom are open and which cartridge is located within the first end of said housing so that said at least one sorbent trap is in fluid communication with the flue gas stream within the stack and a receiving tube within the housing; and
    c) the receiving tube located within said housing having a first end fluidly connected to the cartridge and the at least one sorbent trap and a second end extending from the second end of said housing.

2. The probe of claim 1 wherein there is provided two sorbent traps.

3. The probe of claim 2 wherein at least one of said sorbent traps is divided into three sections, an upstream section, a middle section and a downstream section and wherein each section contains sorbent media, wherein the downstream section is spiked with a known concentration of mercury.

4. The probe of claim 1 wherein the sorbent media is a carbon material.

5. The probe of claim 1 which also contains a high pressure port and a low pressure port at its first end.

6. The probe of claim 1 which also contains a thermocouple wire extending from its first end to past its second end.

7. The probe of claim 1 which also contains a removable cover at its first end for removing and inserting the cartridge containing the one or more sorbent traps.

\* \* \* \* \*